United States Patent [19]

Schmitthenner et al.

[11] Patent Number: 4,758,679

[45] Date of Patent: Jul. 19, 1988

[54] PREPARATION OF 7-(3-(PROPYLAMINO)-2-HYDROXY-PROPOXY)FLAVONE

[75] Inventors: Hans F. Schmitthenner, Honeoye Falls; Edwin S. C. Wu, Rochester, both of N.Y.

[73] Assignee: Pennwalt Corporation, Philadelphia, Pa.

[21] Appl. No.: 887,757

[22] Filed: Jul. 18, 1986

[51] Int. Cl.$^4$ ............................................. C07D 311/30
[52] U.S. Cl. ........................................................ 549/403
[58] Field of Search .......................................... 549/403

[56] References Cited

U.S. PATENT DOCUMENTS

| | | | |
|---|---|---|---|
| 3,450,717 | 6/1969 | Kramer et al. | 549/403 |
| 3,462,455 | 8/1969 | Kramer et al. | 549/403 |
| 3,637,718 | 1/1972 | Kramer et al. | 549/403 |
| 3,993,669 | 11/1976 | Pfister | 549/401 |
| 4,241,069 | 12/1980 | Buckler et al. | 424/263 |
| 4,461,907 | 7/1984 | Batchelor et al. | 549/406 |
| 4,495,198 | 1/1985 | Wu | 514/456 |

FOREIGN PATENT DOCUMENTS 1022745  3/1966  United Kingdom .

OTHER PUBLICATIONS

Indian J. Chem., vol. 13, No. 4, 425, (1975).

*Primary Examiner*—Nicky Chan

[57] ABSTRACT

In a process for preparing 7-[3-(propylamino)-2-hydroxypropoxy]flavone by the reaction of 7-(2,3-epoxypropoxy)flavone and n-propylamine, the improvement which resides in treating the beta-aminochalcone byproduct with a weak organic acid to convert the chalcone to the desired aminated flavone.

4 Claims, No Drawings

PREPARATION OF 7-(3-(PROPYLAMINO)-2-HYDROXYPROPOXY)-FLAVONE

This invention relates to a process for improving the yield of 7-[3-(propylamino)-2-hydroxypropoxy]flavone, particularly when prepared by the process of U.S. Pat. No. 4,495,198.

BACKGROUND

7-[3-(propylamino)-2-hydroxypropoxy]flavone and its acid addition salts are useful as antihypertensive agents as described, for example, in U.S. Pat. No. 4,495,198. In this patent, the specification of which is herein incorporated by reference, the subject compound is shown to have been prepared in about 48% yield from the reaction of 7-(2,3-epoxypropoxy)flavone with n-propylamine. A major by-product of this reaction, and thus a cause of the moderate yields, is the formation of the corresponding beta-aminochalcone due to opening of the pyrone ring. Chalcone formation is well-known and has been reported by researchers such as Zagorevskii et al, Chem. of Heterocyclic Compounds, 7(6), 675 (1971); Baker et al, J. Chem. Soc., 2142 (1949); and Jerzmanowska et al, Monatshefte fuer Chem., 98(4), 1395 (1967).

BRIEF SUMMARY OF THE INVENTION

The present invention relates to an improvement in a process for preparing 7-[3-(propylamino)-2-hydroxypropoxy]flavone via the reaction of 7-(2,3-epoxypropoxy)flavone and n-propylamine whereby the desired flavone product and a corresponding beta-aminochalcone by-product are obtained, the improvement residing in contacting the by-product beta-aminochalcone with a weak organic acid having a pKa of about 1-6 in the presence of an alcoholic solvent to convert said beta-aminochalcone to the desired 7-[3-(propylamino)-2-hydroxypropoxy]flavone.

DETAILED DESCRIPTION

It has now been found that treatment of the beta-aminochalcone by-product, formed during the aforesaid amination reaction, with a weak organic acid such as maleic acid in the presence of an alcoholic solvent such as ethanol will convert a substantial portion of the chalcone to the desired flavone end-product, thereby typically increasing yields of the flavone (as the free base) from about 50% to about 70 to 80%. Strong acids such as hydrochloric acid have been found to be considerably less effective.

As described in U.S. Pat. No. 4,495,198, the 7-(2,3-epoxypropoxy)flavone is normally reacted with a large excess of the n-propylamine at elevated temperature in an alcoholic solvent such as methanol, ethanol, or isopropanol. It is thus advantageous to remove the excess, unreacted propylamine from the resultant reaction mixture prior to treatment with the weak acid in order to avoid neutralization of the acid. The 7-[3-(n-propylamino)-2-hydroxypropoxy]flavone resulting from the reaction of the epoxide and the n-propylamine may also be removed, if desired, prior to treatment with the weak acid, although the in-situ treatment (without flavone removal) is preferred.

The reaction mixture resulting from the amination reaction (after removal, if desired, of excess amine and/or flavone reactant) is contacted with a weak organic acid having a pKa range of from about 1 to about 6 in the presence of an alcoholic solvent. Typical organic acids are those having from about 1 to 7 carbons and 1 to 2 carboxyl groups, such as acetic, oxalic, malonic, maleic, fumaric, succinic, and benzoic acids. Maleic acid is preferred since it not only achieves efficient closure of the beta-aminochalcone ring but also permits easy isolation of the preferred maleate salt form of the flavone product. From about 2 to about 5 molar equivalents of the acid are normally used, per mole of the starting epoxide, although greater amounts also work well. At lower levels of acid the reaction becomes sluggish. In the in-situ embodiment about 5 molar equivalents are preferred, while about 2 to 2.5 molar equivalents are preferred if the flavone product is first removed.

The alcoholic solvent may be any suitable lower alkanol solvent, preferably one having 1 to 5 carbons such as methanol, ethanol, propanol, isopropanol, butanol, or amylol, with ethanol being most preferred. The solvent is generally used in about 6 to 20 volumes (in ml.) per weight (in grams) of the starting epoxide. In the in-situ embodiment about 15 volumes/weight are preferred, while about 7 volumes/weight are preferred if the flavone product is first removed.

The acid treatment step is generally carried out at a temperature of from about 20° to about 100° C., preferably about 60° to 80° C., most preferably about 60° C., although the desired temperature can vary somewhat depending on the specific reaction mixture being treated. The duration of the acid treatment normally ranges from about 1 to about 5 hours, more typically about 2 hours.

Pharmaceutically acceptable addition salts of the 7-[3-(propylamino)-2-hydroxypropoxy]flavone can be prepared by reaction of the flavone with suitable acids such as maleic acid, hydrochloric acid, sulfuric acid, citric acid, methanesulfonic acid, and succinic acid. The maleate salt is preferred.

The invention is further illustrated by the following examples in which all parts and percentages are by weight unless other specified.

EXAMPLE 1

A. Preparation of Flavone As Free Base:

A mixture of 36.7 kg (621 mol) of n-propylamine, 2.62 kg (8.9 mol) of 7-(2,3-epoxypropoxy)flavone, and 74.4 liters of absolute ethanol is stirred and heated at 50°-55° C. for one hour. The mixture is filtered through a celite precoated sparkler filter. The filtrate is concentrated to 20 liters under a reduced pressure of 20-30 mm Hg at 80° C. to give a slurry. The slurry is cooled to 15° C., and the product is filtered off and washed with 4.9 liters of ethanol. The solid obtained is dried for twelve hours at 50° C. and 50 mm Hg to yield 1.72 kg (4.87 mols) of the product 7-[3-(propylamino)-2-hydroxypropoxy]flavone as the base; yield is 54.7% based on the epoxide.

B. Purification of Base:

A solution of the 1.72 kg of 7-[3-(propylamino)-2-hydroxypropoxy]flavone product prepared as described above, 4.9 liters of 95% ethanol and 13.7 liters of water is acidified to pH 1 with aqueous HCl. The aqueous solution is washed with methylene chloride (2×2.31 liters and 4×1.15 liters). The aqueous solution is separated and pressure filtered through a celite coated sparkler filter. The filtrate is slowly basified to a pH greater than about 8 with 3.27 l of 2.5 N sodium hydroxide. The solid that precipitates is filtered off and washed with 11.4 liters of water until the filtrate is neutral. The solid is dried at 50° C. and 60 mm Hg for 17.5 hours to provide 1.59 kg (4.5 mols) of purified base; yield is 50.6% based on the starting epoxide.

C. Maleate Salt of Flavone:

A 30 gallon Pfaudler is charged with 74.7 liters of ethanol and 3.18 kg (8.98 mols) of 7-[3-(propylamino)-2-hydroxypropoxy]flavone. The mixture is warmed to dissolve the free base, 1.29 kg (11.1 mols) of maleic acid are added, and the mixture is heated at reflux to obtain solution. The hot solution is treated with 654 g of charcoal for about 45 minutes and then clarified by filtration through a celite coated sparkler filter. The filtrate is cooled to 30° C., then stirred at room temperature for 20 hours. The solid is collected, washed with 24.9 liters of ethanol and dried at 50° C., 50 mm Hg, for 4 hours to give 3.57 kg (7.6 mols) (84.5%) of the maleate salt.

D. Maleic Acid Recovery Treatment:

The ethanol-propylamine filtrate from the amination reaction is further concentrated under vacuum at 80° C. to remove the solvents and excess amine. About 1.53 kg of residue is obtained, of which about 115 g (corresponding to 196 g (0.67 mol) of epoxide) are dissolved in 1337 ml of absolute ethanol and 188.8 g (1.63 mols) of maleic acid are added. The solution is heated at 60° C. for two hours and then cooled to room temperature. The solution is stirred at room temperature for 16 hours and the precipitated solid is filtered to give 80 grams of the maleate salt. The maleate salt is dissolved in a mixture of 1154 ml water, 385 ml of 95% ethanol, and 154 ml of 2.5N HCl. The solution is extracted with methylene chloride (2×130 ml and 4×50 ml). The aqueous layer is separated and basified with 2.5N NaOH (250 ml) to pH 11. The precipitated base, 56 g of 7-[3-(propylamino)-2-hydroxypropoxy]flavone, is filtered off and air dried. The base is recrystallized from 560 ml of absolute ethanol to give 49.4 g of base (0.14 mol); yield is 20.9% from the epoxide, thus increasing the total yield of free base from 50.6% to 71.5%. The 49.4 g of recrystallized base is then converted to the maleate salt by dissolving it in 1.1 liters of ethanol and treating it with 20 g of maleic acid. The solution is treated with 10 g of charcoal and filtered. The cooled filtrate precipitates as a solid which is separated by filtration to give 57.6 g of the maleate salt (0.12 mol, 88%).

EXAMPLE 2

In-Situ Maleic Acid Treatment:

200 ml of absolute ethanol is mixed with 400 ml n-propylamine (4.87 mol) and the resulting warm solution is cooled to 10° C. followed by the addition, in portions, of 22.2 g (0.0754 mol) of 7-[2,3-epoxypropoxy]flavone. The mixture is heated to 50°-55° C. for 1.5 hours with stirring to give a deep yellow solution which is then cooled, concentrated under reduced pressure (to remove amine), and vacuum dried. (Amination and ring closure monitored by tlc, 10% methanol in methylene chloride, visualized under short and long wave UV light. The chalcone is observed as a slightly higher moving yellow spot vs. blue product under long wave.) The resultant yellow solid, consisting of about 1:1 free base of the product and ring-opened chalcone, is dissolved in 300 ml warm absolute ethanol containing 43.7 g (0.377 mol) maleic acid and heated at 60° C. for 2 hours after which time no chalcone remains (monitored as outlined above). Slow cooling, with stirring, produces off-white crystals which are filtered off, rinsed with 50 ml cool (10° C.) ethanol, and vacuum dried at 70° C.; yield is 31.0 g (0.066 mol), 87.6%. The maleate is extracted to remove trace impurities by the following procedure:

The crude maleate is dissolved with slight warming in 450 ml water and 150 ml 95% ethanol. The solution is acidified to pH 1-2 with 60 ml 2.5 HCl and, after cooling to room temperature, extracted with three 50 ml portions of methylene chloride. Slow addition, with stirring, of 2.5N NaOH into the aqueous layer to pH 10-11 produces a white solid which is stirred several hours to ensure complete precipitation. The white solid (free base) is filtered off, rinsed with two 100 ml portions of water (filtrate pH 9), air dried for several hours, then vacuum dried at 50° C. to a constant weight of 21.7 g (0.0614 mol); 81.4% conversion from the epoxide. A solution of the free base, dissolved by warming in 400 ml absolute ethanol and containing 7.84 g (0.0676 mol) maleic acid is heated to boiling, filtered, and slowly cooled with stirring for two hours. The crystalline white product is collected, rinsed with two 50 ml portions of cool (10° C.) absolute ethanol, air dried, then vacuum dried at 70° C.; yield is 25.6 g (0.0545 mol); 88.8%; 72.3% overall from the epoxide. The maleate is recrystallized from 500 ml of absolute ethanol, filtered, and dried as above; yield is 23.0 g (0.049 mol); 79.8% conversion from the crude base; snow white crystals, m.p. 172°-173° C.

What is claimed is:

1. In a process for preparing 7-[3-(propylamino)-2-hydroxypropoxy]flavone which comprises contacting 7-(2,3-epoxypropoxy)flavone with n-propylamine to obtain the desired 7-[3-(propylamino)-2-hydroxypropoxy]flavone and a corresponding beta-aminochalcone by-product, the improvement which comprises contacting the by-product beta-aminochalcone with maleic acid in the presence of an alcoholic solvent to convert said beta-aminochalcone to the desired 7-[3-(propylamino)-2-hydroxypropoxy]flavone.

2. The process of claim 1 wherein the alcoholic solvent is ethanol.

3. The process of claim 2 wherein any unreacted n-propylamine is removed before contacting the chalcone with maleic acid.

4. The process of claim 3 wherein the 7-[3-(propylamino)-2-hydroxypropoxy]flavone resulting from the reaction of n-propylamine and the epoxide is removed prior to contacting the chalcone with maleic acid.

* * * * *